United States Patent [19]
Reed-Gitomer

[11] Patent Number: 5,192,660
[45] Date of Patent: Mar. 9, 1993

[54] ELISA METHODS FOR THE DETERMINATION OF HUMAN PLATELET DERIVED GROWTH FACTOR (PDGF) DIMER FORMS PRESENT IN HUMAN TISSUES AND FLUIDS

[75] Inventor: Berenice Y. Reed-Gitomer, Washington Grove, Md.

[73] Assignee: The United States of America as represented by the Department of Health and Human Services, Washington, D.C.

[21] Appl. No.: 341,949

[22] Filed: Apr. 24, 1989

[51] Int. Cl.$^5$ .................................. G01N 33/543
[52] U.S. Cl. ........................ 435/7.21; 435/7.24; 435/7.94; 435/962; 435/969; 435/973; 436/518
[58] Field of Search .............. 435/7.94, 962, 969, 435/973, 7.21, 7.24; 436/518

[56] References Cited

U.S. PATENT DOCUMENTS

| | | | |
|---|---|---|---|
| 4,474,892 | 10/1984 | Murad et al. | 436/513 |
| 4,504,585 | 3/1985 | Reynolds | 436/518 |
| 4,818,709 | 4/1989 | Primus et al. | 436/518 |
| 5,094,941 | 3/1992 | Hart | 435/7.9 |

FOREIGN PATENT DOCUMENTS 8200204 1/1982 World Int. Prop. O. .

OTHER PUBLICATIONS

C. E. Hart et al., *Biochemistry*, 29, 166–172, 1990.
A. Voller, in E. T. Maggio (Ed.) *Enzyme-Immunoassay*, CRC Press, Inc. Boca Raton, Fla. 1980. pp. 181–185.

*Primary Examiner*—David Saunders
*Attorney, Agent, or Firm*—Birch, Stewart, Kolasch & Birch

[57] ABSTRACT

Enzyme linked immunosorbent assay (ELISA) methods for quantitatively determining the level of PDGF-BB and PDGF-AB, or, PDGF-AA and PDGF-AB present in a human's bodily fluids, tissue extracts, or a fluid contacting humans cells in culture, are disclosed.

10 Claims, 1 Drawing Sheet

ELISA METHODS FOR THE DETERMINATION OF HUMAN PLATELET DERIVED GROWTH FACTOR (PDGF) DIMER FORMS PRESENT IN HUMAN TISSUES AND FLUIDS

BACKGROUND OF THE INVENTION

Human platelet derived growth factor (PDGF) is composed of a dimer of two homologous polypeptide chains designated A and B. There are 3 dimeric forms AA, AB, and BB, the AB form being the predominant form found in serum, originating from the alpha granule of platelets. A number of tumor cells have been shown to express AA or BB homodimers. Glioma cells express the AA dimer (Nister et al, Cell, 52, 791-799 (1988)), as do osteosarcoma cells (Betsholtz et al, Nature, 320, 695-699). B chain expression is elevated in human atherosclerotic lesions (Barrett and Benditt, Proc. Natl. Acad. Sci., 84, 1099-1103 (1987)) and also in activated human monocytes (Shimakado et al, Cell, 43, 277-285 (1985)) (Martinet et al, Nature, 319, 158-186 (1986)). Accurate quantitation of the various dimeric forms of PDGF may consequently serve as an indicator of pathological conditions. None of the current methods for quantitative assay of PDGF distinguish between the dimeric forms of the molecule and have therefore detected total levels of PDGF. Current methods for assay can be divided into 3 categories.

1) Bioassay based on the ability of PDGF to stimulate 3H thymidine incorporation into fibroblasts such as Swiss mouse 3T3 cells (Deuel et al, J. Biol. Chem., 256, 8896-8899 (1981)). (Kumar et al, FASEB J., 7, 2272-2277 (1988)).

2) Radioreceptor assays utilizing 1251 labelled PDGF as described by Singh et al, J. Cell. Biol., 95, 667-671 (1982), Bowen-Pope and Ross, In control of animal cell proliferation, eds. Boynton and Lefford, Vol. 1, 281-312 (1985); Nister et al, Cell, 52, 791-799 (1988); D. F. Bowen Pope, et al, J. Biological Chemistry Vol. 264, No. 5, pp. 2502-2508 (1989)

3) Enzyme immunoassay (Kumar et al, FASEB J., 7, 2272-2277 (1987)) (Martinet et al, New Engl. J. Med., 317, 202-209 (1988)).

SUMMARY OF THE INVENTION

The present invention provides a quantitative enzyme linked immunosorbent assay (ELISA) for the determination of PDGF's BB, and AB dimer forms present in human bodily fluids, tissue extracts or fluid contacting human cells in culture, and as well, an ELISA method for the determination of PDGF's dimer forms AA and AB present in human bodily fluids, tissue extracts or fluid contacting human cells in culture. In addition to being able to distinguish between dimeric forms of PDGF present in a sample, the methods of the present invention are more sensitive than prior enzyme linked immunosorbent assays utilized to detect PDGF. Furthermore, the methods of the present invention do not necessitate the use of radioactivity and the accompanying disposal problems which occurred when prior radio-receptor assays were utilized.

In a first embodiment, the present invention is directed to an enzyme linked immunosorbent assay for the quantitative determination of human platelet derived growth factor homodimer BB and heterodimer AB, but not homodimer AA, present in human bodily fluid, tissue extracts, or a fluid contacting human cells in culture, which comprises the steps of:

(I) providing an anti-human platelet derived growth factor homodimer BB antibody coated surface on a substrate;

(II) contacting a patient's bodily fluids, tissue extracts, or a fluid contacting said patient's cells in culture with said coated substrate surface to bind human platelet derived growth factor homodimer BB or heterodimer AB present in said patient's bodily fluids, tissue extracts, or fluid contacting said patient's cells in culture to said coated surface;

(III) contacting, after step (II), a second anti-platelet derived growth factor antibody with said coated surface, to bind said second antibody to said coated surface when human platelet derived growth factor homodimer BB or heterodimer AB has previously bound to said coated surface in step II;

(IV) contacting, after step III, an enzyme labeled antibody which is reacted with said second antibody with said coated surface, to bind said enzyme labeled antibody to said coated surface when said second antibody has previously bound to said coated surface in step III; and (V) contacting, after step IV, said coated substrate with a chemical (enzyme label indicator) which indicates the presence of said enzyme labeled antibody bound to said coated surface.

More specifically, the assay comprises the steps of:

(I) providing an animal(1) anti-human platelet derived growth factor homodimer BB antibody coated surface on a substrate;

(II) contacting a patient's bodily fluids, tissue extracts, or fluid contacting said patient's cells in culture with said coated substrate surface to bind human platelet derived growth factor homodimer BB or heterodimer AB present in said patient's bodily fluids, tissue extracts, or fluid contacting said patient's cells in culture to said coated surface;

(III) contacting, after step (II), an animal(2) anti-human platelet derived growth factor antibody with said coated surface, to bind said animal(2) anti-human antibody to said coated surface when human platelet derived growth factor homodimer BB or heterodimer AB has previously bound to said coated surface in step II;

(IV) contacting, after step III, an animal(3) anti-animal(2) enzyme labelled antibody with said coated surface to bind said enzyme labelled animal(3) anti-animal(2) antibody to said coated surface when said animal(2) anti-human antibody has previously bound to said coated surface in step III; and (V) contacting, after step IV, said coated substrate with a chemical enzyme label indicator which indicates the presence of said animal(3) anti-animal(2) enzyme labelled antibody bound to said coated surface.

In a second embodiment, the present invention is directed to an enzyme linked immunosorbent assay for the quantitative determination of human platelet derived growth factor heterodimer AB and homodimer AA, but not homodimer BB, present in human bodily fluid, tissue extracts, or a fluid contacting human cells in culture, which comprises the steps of:

(I) providing an anti-human platelet derived growth factor homodimer AA antibody coated surface on a substrate;

(II) contacting a patient's bodily fluids, tissue extracts, or a fluid contacting said patient's cells in culture with said coated substrate surface to bind human platelet derived growth factor heterodimer AB and homodimer AA present in said patient's bodily fluids, tissue extracts, or a fluid contacting said patient's cells in culture, to said coated surface;

(III) contacting, after step (II), a second anti-human platelet derived growth factor antibody with said coated surface, to bind said second anti-human antibody to said coated surface when human platelet derived growth factor heterodimer AB or homodimer AA has previously bound to said coated surface in step II;

(IV) contacting, after step III, an enzyme labelled antibody which is reactive with said second antibody with said coated surface, to bind said enzyme labelled antibody to said coated surface when said second antibody has previously bound to said coated surface in step III; and (V) contacting, after step IV, said coated substrate with a chemical enzyme label indicator which indicates the presence of said enzyme labelled antibody bound to said coated surface. More specifically, the assay comprises the steps of:

(I) providing an animal(1) anti-human platelet derived growth factor homodimer AA antibody coated surface on a substrate:

(II) contacting a patient's bodily fluids, tissue extracts, or a fluid contacting said patient's cells in culture with said coated substrate surface to bind human platelet derived growth factor heterodimer AB and homodimer AA present in said patient's bodily fluids, tissue extracts, or a fluid contacting said patient's cells in culture to said coated surface;

(III) contacting, after step II, an animal(2) anti-human platelet derived growth factor antibody with said coated surface, to bind said animal(2) anti-human antibody to said coated surface when human platelet derived growth factor heterodimer AB or homodimer AA has previously bound to said coated surface in step II;

(IV) contacting, after step III, an animal(3) anti-animal(2) enzyme labelled antibody with said coated surface, to bind said enzyme labelled mammal(3) anti-animal(2) antibody to said coated surface when said animal(2) anti-human antibody has previously bound to said coated surface in step III; and (V) contacting, after step IV, said coated substrate with a chemical enzyme label indicator which indicates the presence of said animal(3) anti-animal(2) enzyme labelled antibody bound to said coated surface.

It is also provided herein that by utilizing each of the above provided assays [i.e., Assay for PDGF-AA and AB, and Assay for PDGF-BB and AB] one can quantitatively determine the level of PDGF-AA, PDGF-BB, and PDGF-AB in a sample, whenever it is known or believed the sample only contains quantitatively determinable levels of 2 of the 3 possible PDGF dimer forms. The procedure utilized involves testing portions of a homogenous sample by each of the above two methods provided herein, and determining by difference (when significant differences are obtained) the amount and type of each PDGF dimer present. The technique thus provided should be readily understood by those skilled in the art, inasmuch as it is known that a PDGF-AA coated surface will not bind PDGF-BB; a PDGF-BB coated surface will not bind PDGF-AA; and that both a PDGF-AA and PDGF-BB coated surface will bind PDGF-AB.

BRIEF DESCRIPTION OF THE DRAWINGS

In FIG. 1, symbol No. 1 indicates alkaline phosphatase conjugated anti-goat antibody, symbol No. 2 indicates goat anti-platelet derived growth factor antibody, symbol No. 3 indicates platelet derived growth factor, symbol No. 4 indicates rabbit anti-platelet derived growth factor antibody, and symbol No. 5 indicates a substrate plate.

DETAILED DESCRIPTION OF THE INVENTION

Figure 1:
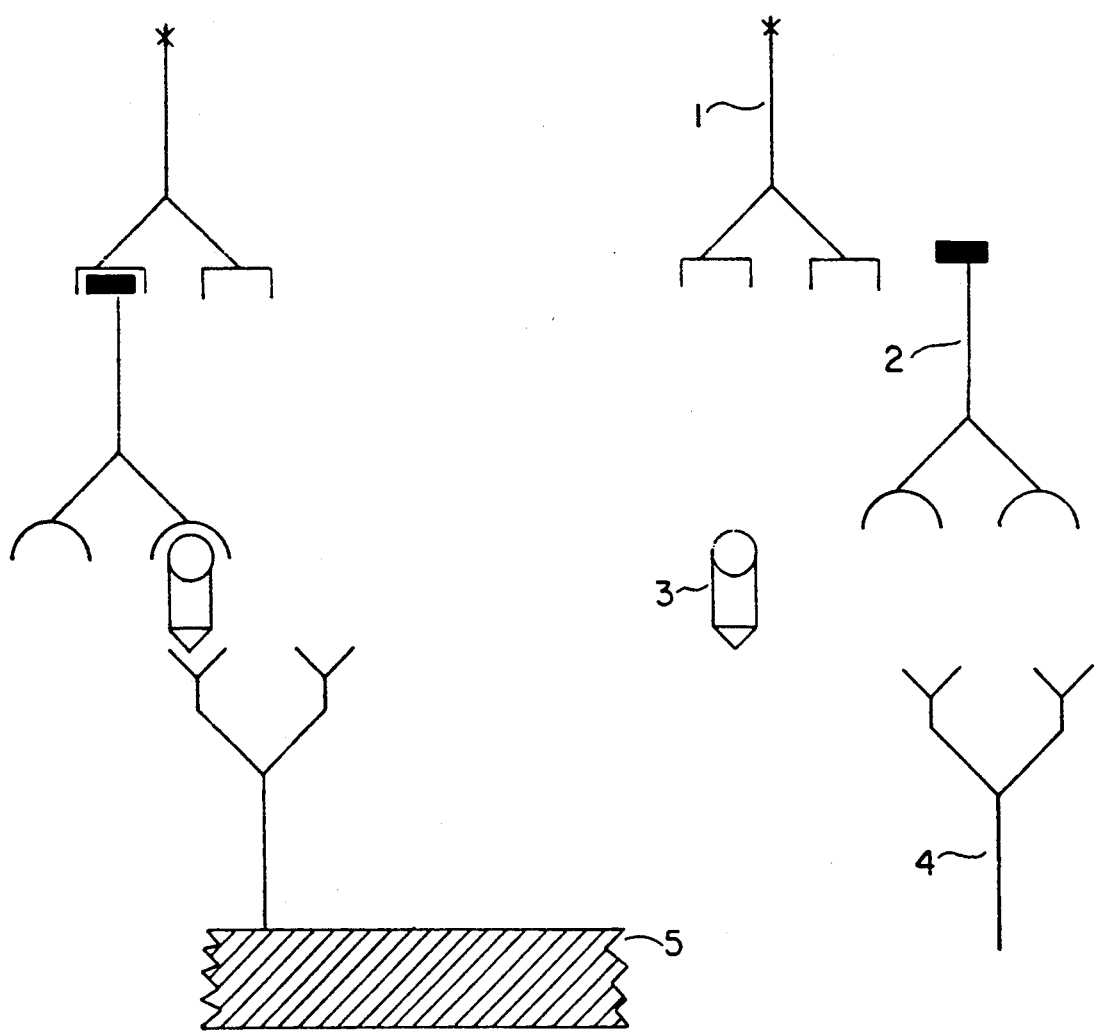
FIG. 1 is a schematic representation of the enzyme linked immunosorbent assay, utilized in Examples I, II and III.

The term "animal(1)" as used herein refers to a mammalian species other than homo sapien.

The term "animal(2)" as used herein refers to a mammalian species other than homo sapiens and that mammalian species chosen as animal(1).

The term "animal(3)" as used herein refers to a homo sapien or a mammalian creature other than that mammalian creature chosen as animal(2).

The term "substrate" as used herein refers to a polystyrene surface having high binding capacity, or the like, to which an animal(1) anti-human platelet derived growth factor homodimer AA or homodimer BB antibody can attach.

The term "enzyme labelled antibody" as used herein refers to an antibody labelled with an enzyme such as alkaline phosphatase, peroxidase, or the like, which is capable of reaction with a chemical indicator as defined below.

The term "enzyme label indicator" as used herein refers to chemical indicators for indicating, preferably by color change, the presence of enzyme labelled antibody bound to the substrate's coated surface. For example, p-nitrophenol phosphate is one such enzyme label indicator for the enzyme alkaline phosphatase.

The term "Tris" as used herein means 2-amino-2-hydroxymethyl-1,3-propanediol.

The term "coating buffer solution" as used herein refers to the solution (10 mM Tris/HCl pH 8.5 and 100 mM NaCl), and the like.

The term "blocking solution" as used herein refers to 1% casein in tris buffered saline (TBS) (0.02M Tris/HCl pH 7.4, 0.14M NaCl, 0.003M KCl) and like solutions.

The term "antibody diluent" refers to 10% bovine serum albumin (which does not contain detectible levels of PDGF) in TBS.

The term "standard diluent" refers to 2.5% BSA in TBS containing 10% v/v "negative plasma".

The term "wash buffer" or "wash solution" as used herein refers to tris buffered saline (TBS) (0.02M Tris/HCl pH 7.4 0.14M NaCl, 0.003M KCl) containing 0.05% of the surfactant Tween 20 (Tween 20 is commercially available from Bio-Rad), and the like.

The term "antibody" as used herein refers to polyclonal antibodies or monoclonal antibodies. Although polyclonal antibodies are preferred, monoclonal antibodies having appropriate binding ability to the desired "antigens" may be substituted therefor.

The term "bodily fluid" refers to any human liquid product as for example plasma, peritoneal fluid, cerebrospinal fluid and so forth.

The term "negative plasma" as used herein refers to platelet poor plasma, and which plasma when tested by ELISA assay, has a total PDGF content of less than 50 pg/ml.

The term "platelet poor plasma" as used herein refers to that fraction of whole blood collected in such manner as to ensure the absence of platelets or activation of same. A suitable method for obtaining platelet poor plasma would be to collect whole blood into tubes containing 5 mM sodium EDTA (ethylenediamine tetraacetic acid) and 0.67 units/ml of bovine lung aprotinin (Sigma), mix contents thoroughly and gently by several inversions. Allow tubes to sit on ice for no less than 15 min and no longer than 2 hours and centrifuging for 10 min at 2500 g to sediment the cellular fraction. Remove the supernatant to a second polypropylene tube and recentrifuge at 2500 g for 15 min. The supernatant at this stage constitutes platelet poor plasma. To ensure no leakage of platelet contents samples of the plasma may be tested for the presence of a second platelet derived protein such as platelet factor 4 by radio-immunoassay (Abbott labs). It should be understood, of course, that platelet poor plasma may be prepared by other suitable methods without departing from the scope of the present invention.

The terms "fluid contacting human cells in culture" or "fluid contacting said patient's cells in culture" as used herein refers to any culture medium in which human cells have grown or been bathed, prepared as for example by the method described by Kumar et al, FASEB J., 7, 2272-2277 (1985) for the preparation of macrophage conditioned medium. An alternate method is described by Nister et al, 52, 791-799 (1988) for the preparation of glioma conditioned medium or any other suitable technique. Neither of these techniques of preparation, however, should be construed to limit the present invention.

The enzyme linked immunosorbent assay (ELISA) methods provided herein, each consist of multiple steps, and the following is a description of the general methodology utilized in performing those steps. The description is not to be construed as limiting the present invention, however, inasmuch as minor adjustments and/or changes in the methodology of the present invention may be made without departing from the scope of the invention disclosed herein. It is particularly noted that the present invention is construed to include those instances in which one skilled in the art may utilize different but equivalent substrate types, animal antibody types, enzyme labels, enzyme label indicators, coating solutions, blocking solutions and wash solutions, to those disclosed herein.

The first step in the ELISA methods for detecting PDGF-BB and PDGF-AB, or, PDGF-AA and PDGF-AB present in human bodily fluids, tissue extracts, or a fluid contacting human cells in culture involves coating a suitable substrate with a coating of either (a) an animal(1) anti-human PDGF-BB antibody if one desires to detect PDGF-BB and PDGF-AB, or (b) an animal(1) anti-human PDGF-AA antibody if one desires to detect PDGF-AA and PDGF-AB.

In Example I, rabbit polyclonal anti-human PDGF-BB IgG antibody (commercially available from Genzyme Corp.) was utilized, and in Examples II and III, rabbit polyclonal anti-human PDGF-AA IgG antibody (also available commercially from Genzyme Corp.) was utilized. The preferred embodiment of the present invention, thus, utilizes a rabbit as its animal(1), due primarily to the commercial availability of the two above-identified antibodies. It is also noted, that in the preferred embodiment of the present invention one would denature and desalt the anti-human PDGF BB antibody as is done in Examples I and II before coating a substrate, in order to provide a purer coating.

In the preferred embodiment disclosed herein, the substrate coated in the first step is polystyrene, having high binding capacity, with the polystyrene substrate configuration being a plate having multiple wells, since in these wells, test solutions as well as sample standard solutions for constructing a standard curve may be added. In a preferred embodiment of performing the first step, the antibody coated substrate is blocked with a blocking solution. One such blocking solution provided in the present invention is 1% casein in tris buffer saline. A preferred embodiment of the present invention also allows for washing the polystyrene substrate with a wash solution, both after coating the plate with desired animal (I) anti-human antibody and allowing the plate to incubate, and after blocking the coated substrate and allowing the plate to incubate. For these purposes and others the present invention provides a wash solution containing tris buffer saline and the surfactant Tween 20 (Tween 20 is available from Bio Rad).

It is also advantageous, and desirable for one practicing the present invention, to bring into contact with the coated substrate surface, subsequent to step 1 of the ELISA methods provided herein, a standard diluent containing a negative control in order to reduce nonspecific background binding by blocking such surfaces with plasma proteins in negative controls.

The second step in the ELISA methods of the present invention involve contacting a patient's bodily fluids, tissue extracts, or a fluid contacting said patient's cells in culture for the PDGF dimers (the antigens), with an antibody coated plate provided in step (I) of each ELISA method. In the preferred embodiment of the present invention blanks and standard solutions of either PDGF-BB (commercially available from Genzyme Corp.), PDGF-AB (commercially available from Collaborative Research, Inc.), or PDGF-AA (prepared according to the method of Heldin et al, Nature, 319, p. 511-515 (1986), depending on which dimers are to be detected, are also contacted with the coated surface of the substrate, in order to later construct a standard curve by a method similar to that taught by Kumar et al, FASEB J., 7, p. 2272-2277 (1987).

After step 2, in a preferred embodiment of the present invention, to blanks and standard samples are also added a standard diluent solution, test samples are adjusted to a final 1.5% BSA content by addition of a concentration BSA solution in TBS. A preferred embodiment of the invention also allows for washing the coated substrate with a wash solution, as provided in step (I), after a period of incubation.

In the third step of the ELISA methods of the present invention, an animal(2) anti-human PDGF antibody is brought in contact with the coated plate. The PDGF dimer serves as an antigen for this antibody. In Examples I, II and III, herein, goat-anti-human polyclonal antiserum (commercially available from Collaborative Research, Inc.) is utilized, and thus a goat is a preferred animal(2), given the commercial availability of this antibody. A preferred embodiment of the present invention allows for washing the coating substrate with a wash solution, as provided in step (I), above, after a proper period of incubation between the animal(2) anti-human PDG polyclonal antibody and the substrate coating.

In the fourth step of the ELISA methods of the present invention, disclosed herein, an animal(3) anti-animal(2) enzyme labelled antibody is contacted with the coated substrate. The animal(2) anti-human PDGF antibody serves as an antigen for this antibody. In Example I, II and III, disclosed herein, donkey anti-goat IgG alkaline phosphatase conjugated antibody (commercially available from Chemicon) was utilized. Thus, a preferred animal(3) in the present invention is a donkey, given the commercial availability of the above enzyme labeled antibody. As with earlier steps, a preferred embodiment of the present invention allows for washing the substrate coating with a wash solution, as provided in step (I), after a period of incubation between the animal(3) anti-animal(2) enzyme labelled antibody and the substrate coating.

In step V of the ELISA methods of the present invention, a chemical enzyme label indicator is brought in contact with the substrate coating. The chemical indicator is utilized to indicate the presence of animal(3) anti-animal(2) enzyme labelled antibody present on the substrate coating. In Examples I, II and III of the present invention, p-nitrophenol phosphate (commercially available from Kirkegaard and Perry) was utilized in a 10% w/w solution of diethanolamine/HCl buffer, pH 9.8, containing 0.01% of magnesium chloride, to indicate animal(3) anti-animal(2) enzyme labeled antibody present on the substrate coating. It should be understood that the preferred chemical enzyme indicator to use in either ELISA method will depend, of course, on what enzyme labelled antibody has been utilized in step IV.

The following Preparation and Examples provide further illustration of the ELISA methods of the present invention. Certain preferred embodiments of carrying out the present invention are disclosed in the Preparation and Examples, as should be evident to those skilled in the art upon review of the Preparation and Examples.

PREPARATION I

Test Serum Samples

In each of the following Examples I, II and III, test serum samples utilized were identical. Test serum samples came from normal patients showing no signs of pathological diseases which might cause to be produced in the body PDGF-AA or PDGF-BB homodimers. Therefore, it is assumed that the only dimer form of PDGF present in test serum which is quantitatively determinable (i.e., >50 pg/ml) is PDGF-AB.

EXAMPLE I

ELISA Assay for Human Platelet Derived Growth Factor BB and AB

Plate Coating

Rabbit polyclonal anti-PDGF BB IgG (Genzyme Corporation Cat. #ZP 215) is first denatured at a protein concentration of 10 µg/ml by incubating for 10 min at room temperature in 50 mM Glycine/HCl pH 2.5, containing 100 mM NaCl then neutralized with 1M Tris base. The denatured antibody is then desalted by passing the solution over a Sephadex PD 10 column (Pharmacia PL) equilibrated in the coating buffer solution (10 mM Tris/HCl pH 8.5 containing 100 mM NaCl) the sample is eluted from the column in the same buffer. The solution is adjusted to a protein concentration of 2 µg/ml by dilution in coating buffer and 200 µl added to each well on a polystyrene microtiter plate (NUNC Immuno flat bottomed well). The plate is incubated at 37° for 2h in a humid atmosphere contents decanted and wells washed 4 times with 250 µl/well of Tris buffered saline (TBS) (0.02M Tris/HCl pH 7.4, 0.14M NaCl, 0.003M KCl) containing 0.05% Tween 20 (Bio-Rad) (wash buffer). The wells are blocked with 250 µl of 1% casein in TBS (blocking solution) by incubating overnight at 4° followed by 6 washings in wash buffer.

Assay

A standard curve within the range 50–10000 pg/ml is prepared by diluting PDGF BB standard (Genzyme) in standard diluent solution containing 10% of a control negative plasma sample (having PDGF concentration<50 pg/ml) when human plasma or serum samples are to be assayed, care being taken to neutralize any acetic acid remaining in the PDGF standard, and 200 µl added to each of the designated standard wells on the microtiter plate. Unknown samples were diluted as appropriate in diluent solution and 180 µl added to the test wells. When human plasma or serum samples are to be assayed 20 µl of 15% BSA in TBS is added to all samples, this amount has been shown to be sufficient to correct for any false positive results due to non-specific binding of plasma proteins. The plate is incubated for 2h at 37° in a humid atmosphere. The plate is washed 6 times in wash buffer and 200 µl of Goat anti-human PDGF polyclonal antiserum (Collaborative Research Inc.) at a dilution of 1/500 in 1% BSA in TBS, of a 10 mg/ml solution added to each well. The plate is incubated at 37° for 2 h as previously and then washed 6 times in TBS tween. PDGF is detected by addition of 200 µl of a 1/5000 dilution of a donkey anti-goat IgG alkaline phosphatase conjugated antibody prepared in antibody diluent (Chemicon) and incubated for 1.5 h at room temperature followed by 6 standard washes of the plate. Enzyme activity is revealed by addition of 200 µl of a 1 mg/ml solution of p-nitrophenol phosphate (Kirkegaard and Perry) prepared in 10% w/w diethanolamine/HCl buffer pH 9.8 containing 0.01% $MgCl_2$ to each well. The plate is incubated at room temperature until the desired color development is reached, longer incubation periods being necessary to detect lower concentration ranges, i.e., standards less than 1000 pg/ml. Optical densities of standards, as well as that of samples, are determined following addition of 10 µl of 10 mM cysteine stop solution to each well, and by reading at 410 nM. A standard curve is fitted to the points. The concentration of unknown samples such as plasma are determined by comparison of their optical density to the standard curve. Standard optical densities are contained in Table I.

EXAMPLE II

ELISA Assay for Human Platelet Derived Growth Factor AB and BB

Plate Coating

Rabbit polyclonal anti-PDGF BB IgG (Genzyme Corporation Cat. #ZP 215) is first denatured at a protein concentration of 10 µg/ml by incubating for 10 min at room temperature in 50 mM Glycine/HCl pH 2.5, containing 100 mM NaCl then neutralized with 1M Tris base. The denatured antibody is then desalted by passing the solution over a Sephadex PD 10 column (Pharmacia PL) equilibrated in the coating solution (10 mM Tris/HCl pH 8.5 containing 100 mM NaCl) the sample is eluted from the column in the same buffer. The solution is adjusted to a protein concentration of 2 μg/ml by dilution in coating buffer and 200 μl added to each well on a polystyrene microtiter plate (NUNC Immuno flat bottomed well). The plate is incubated at 37° for 2h in a humid atmosphere contents decanted and wells washed 4 times with 250 μl/well of Tris buffered saline (TBS) (0.02M Tris/HCl pH 7.4, 0.14M NaCl, 0.003M KCl) containing 0.05% Tween 20 (Bio-Rad) (wash buffer). The wells are then blocked with 250 μl of 1% casein in TBS (blocking solution) by incubating overnight at 4° followed by 6 washings in wash buffer.

Assay

A standard curve within the range 50–10000 pg/ml is prepared by diluting PDGF AB (Collaborative Research Inc.) in standard diluent solution, care being taken to neutralize any acetic acid remaining in the PDGF standard, and 200 μl added to each of the designated standard wells on the microtiter plate. Unknown samples are diluted as appropriate in antibody diluent and 180 μl added to the test wells. When human plasma or serum samples are to be assayed 20 μl of 15% BSA in TBS is added to all samples, this amount has been shown to be sufficient to correct for any false positive results due to the presence of plasma proteins. The plate is incubated for 2h at 37° in a humid atmosphere. The plate is washed 6 times in wash buffer and 200 μl of Goat anti-human PDGF polyclonal antiserum (Collaborative Research Inc.) at a dilution of 1/500 of a 10 mg/ml solution added to each well. The plate is incubated at 37° for 2h as previously and then washed 6 times in TBS tween. PDGF is detected by addition of 200 μl of a 1/5000 dilution of a donkey anti-goat IgG alkaline phosphatase conjugated antibody (Chemicon) and incubated for 1.5 h at room temperature followed by 6 standard washes of the plate. Enzyme activity is revealed by addition of 200 μl of a mg/ml solution of p-nitrophenol phosphate (Kirkegaard and Perry) prepared in 10% w/w diethanolamine/HCl buffer pH 9.8 containing 0.01% MgCl$_2$ to each well. The plate is incubated at room temperature until the desired color development is reached, longer incubation periods being necessary to detect lower concentration ranges, i.e., standards less than 1000 pg/ml. Optical densities of standards, as well as samples, are determined following addition of 10 μl of 10 mM cysteine stop solution to each well. A standard curve is fitted to the points. The concentration of unknown samples such as plasma are determined by comparison of their optical density to the standard curve. Standard optical densities are contained in Table I.

EXAMPLE III

ELISA Assay for Human PDGF AB and AA

Plate Coating

Polystyrene microtiter plates (NUNC Immuno flat bottomed) are coated directly with 200 μl/well of non-denatured rabbit Anti-human PDGF homodimer AA IgG (Genzyme Corporation Cat. #ZP 214) at a concentration of 4 μg/ml in coating buffer. The plates are incubated and washed as described in Example II.

Assay

A standard curve within the range 50–10,000 pg/ml is prepared by diluting PDGF (AB) (Collaborative Research Inc.) or PDGF-AA (prepared as described by Heldin et al, Nature, 319, p. 511–515 (1986)), in standard diluent solution, care being taken to neutralize any acetic acid in the standard. The remainder of the assay proceeds as described in Example II, except that PDGF is detected by addition of 200 μl of a 1/10,000 dilution of Chemicon donkey anti-goat IgG alkaline phosphatase conjugated antibody. Standard optical densities are contained in Table I.

TABLE I

| | STANDARD OPTICAL DENSITIES | | |
|---|---|---|---|
| Concentration | Example I PDGF-AB & BB | Example II PDGF-AB & BB[1] | Example III PDGF-AB & AA[2] |
| 50 pg/ml | 0.041 | 0.095[3] | 0.02 |
| 125 pg/ml | — | — | 0.08 |
| 500 pg/ml | — | — | 0.31 |
| 1000 pg/ml | 0.67 | 0.624 | 0.38 |
| 2000 pg/ml | — | — | 0.73 |
| 4000 pg/ml | 1.10 | 1.393 | 1.15 |

[1]Human Plasma Total AB assayed by this ELISA mean = 524 pg/ml Range 0–1650 pg/ml (N = 6).
[2]Human Plasma Total AB assayed by this ELISA mean = 425 pg/ml (range 0–1100) (N = 6).
[3]Blank subtracted.

Discussion of Results

Test results obtained in Examples II and III, above, and contained in Table I, showed no significant difference in the PDGF-AA and AB, or PDGF-BB and AB values obtained. The non-significance of this difference, between the two results of Examples II and III, provides evidence that the initial assumption in Preparation I was correct (i.e., that test samples from normal patients should not contain a quantifiably determinable amount of either PDGF-BB or AA).

It should be understood that the scope of the present invention is to be limited only by the appended claims.

What is claimed is:

1. An enzyme linked immunosorbent assay for the quantitative determination of human platelet derived growth factor homodimer BB and heterodimer AB present in human bodily fluids, tissue extracts, or a fluid contacting human cells in culture, which comprises the steps of:

(I) providing an anti-human platelet derived growth factor homodimer BB polyclonal antibody coated surface;

(II) contacting a test sample of a patient's bodily fluid, tissue extract or a fluid contacting said patient's cells in culture, with said coated surface to bind human platelet derived growth factor homodimer BB or heterodimer AB present in said patient's bodily fluids, tissue extracts, or a fluid contacting said patient's cells in culture, to said coated surface;

(III) contacting, after step II, a second anti-platelet derived growth factor polyclonal antibody with said coated surface, to bind said second antibody to said coated surface when human platelet derived growth factor homodimer BB or heterodimer AB has previously bound to said coated surface in step II;

(IV) contacting after step III, an enzyme labelled antibody, which is reacted with said second antibody, with said coated surface to bind said enzyme labelled antibody to said coated surface when said second antibody has previously bound to said coated surface in step III;

(V) contacting after step IV, said coated surface with a chemical enzyme label indicator which indicates the presence of said enzyme labeled antibody bound to said coated surface; and (VI) quantitatively determining the amount of said human platelet derived growth factor homodimer BB and heterodimer AB which are present in the test sample based on the amount of the enzyme labelled antibody bound to the coated surface.

2. The assay of claim 1, which comprises the steps of:
(I) providing an animal (1) anti-human platelet derived growth factor homodimer BB polyclonal antibody coated surface;
(II) contacting a test sample of a patient's bodily fluids, tissue extracts or a fluid contacting said patient's cells in culture, with said coated surface to bind human platelet derived growth factor homodimer BB or heterodimer AB present in said patient's bodily fluids, tissue extracts, or a fluid contacting said patient's cells in culture, to said coated surface;
(III) contacting after step II, an animal (2) anti-human platelet derived growth factor polyclonal antibody with said coated surface, to bind said animal (2) anti-human antibody to said coated surface when human platelet derived growth factor homodimer BB or heterodimer AB has previously bound to said coated surface in step II;
(IV) contacting after step III, an animal (3) anti-body (2) enzyme labelled antibody with said coated surface, to bind said enzyme labelled mammal (3) anti-animal (2) antibody to said coated surface when said animal (2) anti-human antibody has previously bound to said coated surface in step III;
(V) contacting after step IV, said coated substrate with a chemical enzyme label indicator which indicates the presence of said animal (3) anti-animal (2) enzyme labeled antibody bound to said coated surface; and
(VI) quantitatively determining the amount of said human platelet derived growth factor homodimer BB and heterodimer AB which are present in the test sample based on the amount of the enzyme labelled antibody bound to the coated surface.

3. The assay of claim 2, wherein a negative plasma is contacted with said coated surface, after step I, in order to reduce non-specific background binding, by blocking such sites on the coated surface with plasma proteins.

4. The assay of claim 2, wherein the amount of said human platelet derived growth factor homodimer BB or heterodimer AB present in the test sample is quantitatively determined in step VI based on the amount of the enzyme labelled antibody which is bound to the coated surface, through a comparison of the test sample with a standard curve prepared for human platelet derived growth factor heterodimer AB.

5. The assay of claim 1, wherein the amount of said human platelet derived growth factor homodimer BB or heterodimer AB present in the test sample is quantitatively determined in step VI based on the amount of the enzyme labelled antibody which is bound to the coated surface, through a comparison of the test sample with a standard curve prepared for human platelet derived growth factor heterodimer AB.

6. An enzyme linked immunosorbent assay for the quantitative determination of human platelet derived growth factor heterodimer AB and homodimer AA present in human bodily fluid, tissue extracts, or a fluid contacting human cells in culture, which comprises the steps of:
(I) providing an anti-human platelet derived growth factor homodimer AA polyclonal antibody coated surface;
(II) contacting a test sample of a patient's bodily fluids, tissue extracts or a fluid contacting said patient's cells in culture, with said coated surface to bind human platelet derived growth factor heterodimer AB or homodimer AA present in said patient's bodily fluids, tissue extracts, or a fluid contacting said patient's cells in culture, to said coated surface;
(III) contacting after step II, a second anti-human platelet derived growth factor polyclonal antibody with said coated surface, to bind said second anti-human antibody to said coated surface when human platelet derived growth factor heterodimer AB or homodimer AA has previously bound to said coated surface in step II;
(IV) contacting after step III, an enzyme labelled antibody which is reactive with said second antibody enzyme labelled antibody to said coated surface when said second anti-human antibody has previously bound to said coated surface in step III;
(V) contacting after step IV, said coated substrate with a chemical enzyme label indicator which indicates the presence of said enzyme labeled antibody bound to said coated surface; and
(VI) quantitatively determining the amount of said human platelet derived growth factor homodimer AA and heterodimer AB which is present in the test sample based on the amount of the enzyme labelled antibody bound to the coated surface.

7. The assay of claim 6, which comprises the steps of:
(I) providing an animal (1) anti-human platelet derived growth factor homodimer AA polyclonal antibody coated surface;
(II) contacting a test sample of a patient's bodily fluids, tissue extracts or a fluid contacting said patient's cells in culture, with said coated surface to bind human platelet derived growth factor heterodimer AB and homodimer AA present in said patient's bodily fluids, tissue extracts, or a fluid contacting said patient's cells in culture, to said coated surface;
(III) contacting after step II, an animal (2) anti-human platelet derived growth factor polyclonal antibody with said coated surface, to bind said animal (2) anti-human antibody to said coated surface when human platelet derived growth factor heterodimer AB or homodimer AA has previously to said coated surface in step II;
(IV) contacting after step III, an animal (3) anti-animal (2) enzyme labelled antibody with said coated surface, to bind said enzyme labelled animal (3) anti-animal (2) antibody to said coated surface when said animal (2) anti-human antibody has previously bound to said coated surface in step III;
(V) contacting after step IV, said coated substrate with a chemical enzyme label indicator which indicates the presence of said animal (3) anti-animal (2) enzyme labelled antibody bound to said coated surface; and
(VI) quantitatively determining the amount of said human platelet derived growth factor homodimer AA and heterodimer AB which is present in the test sample based on the amount of the enzyme labelled antibody bound to the coated surface.

8. The assay of claim 7, wherein a negative plasma is contacted with said coated surface, after step I, in order to reduce non-specific background binding, by blocking such sites on the coated surface with plasma proteins.

9. The assay of claim 7, wherein the amount of said human platelet derived growth factor homodimer AA or heterodimer AB present in the test sample is quantitatively determined in step VI based on the amount of the enzyme labelled antibody which is bound to the coated surface, through a comparison of the test sample with a standard curve prepared for human platelet derived growth factor heterodimer AB.

10. The assay of claim 6, wherein the amount of said human platelet derived growth factor homodimer AA or heterodimer AB present in the test sample is quantitatively determined in step VI based on the amount of the enzyme labelled antibody which is bound to the coated surface, through a comparison of the test sample with a standard curve prepared for human platelet derived growth factor heterodimer AB.

* * * * *